United States Patent [19]
Bates

[11] Patent Number: 5,944,728
[45] Date of Patent: Aug. 31, 1999

[54] SURGICAL RETRIEVAL BASKET WITH THE ABILITY TO CAPTURE AND RELEASE MATERIAL

[75] Inventor: James S. Bates, Bloomington, Ind.

[73] Assignee: Boston Scientific Corporation, Natick, Mass.

[21] Appl. No.: 09/064,997

[22] Filed: Apr. 23, 1998

[51] Int. Cl.⁶ .................................................. A61B 17/22
[52] U.S. Cl. .......................... 606/127; 606/128; 606/106; 606/206; 606/200; 604/264; 604/265
[58] Field of Search .................................. 606/127, 128, 606/106, 206, 2.5, 113, 200; 604/264, 265

[56] References Cited

U.S. PATENT DOCUMENTS

| | | | |
|---|---|---|---|
| 3,137,298 | 6/1964 | Glassman | 128/328 |
| 3,472,230 | 10/1969 | Fogarty . | |
| 3,828,790 | 8/1974 | Curtiss et al. | 128/320 |
| 3,955,578 | 5/1976 | Chamness et al. | 128/303.15 |
| 4,046,150 | 9/1977 | Schwartz et al. | 128/328 |
| 4,198,960 | 4/1980 | Utsugi | 128/6 |
| 4,243,040 | 1/1981 | Beecher | 128/328 |
| 4,299,225 | 11/1981 | Glassman | 128/328 |
| 4,326,530 | 4/1982 | Fleury, Jr. | 128/303.14 |
| 4,347,846 | 9/1982 | Dormia | 128/328 |
| 4,425,908 | 1/1984 | Simon | 128/1 R |
| 4,447,227 | 5/1984 | Kotsanis | 604/95 |
| 4,557,255 | 12/1985 | Goodman | 128/7 |
| 4,590,938 | 5/1986 | Segura et al. | 128/328 |
| 4,611,594 | 9/1986 | Grayhack et al. | 128/328 |
| 4,612,931 | 9/1986 | Dormia | 128/328 |
| 4,625,726 | 12/1986 | Duthoy | 128/328 |

(List continued on next page.)

FOREIGN PATENT DOCUMENTS

| | | |
|---|---|---|
| 56865/86 | 9/1985 | Australia . |
| 0 195 444 | 3/1985 | European Pat. Off. . |
| 0 428 998 A1 | 5/1991 | European Pat. Off. . |
| 0 737 450 A1 | 10/1996 | European Pat. Off. . |
| 2159 | 6/1927 | France ................................. 606/127 |
| 2821048 | 11/1979 | Germany . |
| 3213223 A1 | 10/1983 | Germany . |
| 3407708 A1 | 9/1985 | Germany . |
| 3620385 C1 | 1/1988 | Germany . |
| 3633527 A1 | 4/1988 | Germany . |
| 4025799 A1 | 2/1992 | Germany . |
| 2 020 557 | 11/1979 | United Kingdom . |
| WO 91/11209 | 8/1991 | WIPO . |
| 92/05828 | 4/1992 | WIPO . |
| WO 94/24946 | 11/1994 | WIPO . |
| 95/05129 | 2/1995 | WIPO . |
| WO 96/01591 | 1/1996 | WIPO . |

OTHER PUBLICATIONS

Vorwerk, Dierk et al., "Percutaneous Embolectomy: In Vitro Investigations of the Self–expanding Tulip Sheath[1]", RSNA, Feb. 1992.

Vorwerk, Dierk et al., "Percutaneous Ballon Embolectomy with a Self–expanding Tulip Sheath: In Vitro Experiments", RSNA, Oct. 1995.

*Primary Examiner*—Michael Buiz
*Assistant Examiner*—Lien Ngo
*Attorney, Agent, or Firm*—Testa, Hurwitz & Thibeault, LLP

[57] ABSTRACT

A surgical extractor, and related method, for removing material (such as calculi and stones) from the body has the ability to capture and release material. The extractor has a sheath, a basket comprised of a plurality of legs that are unattached at a distal end of the basket and joined at a proximal base of the basket, and a plunger at the distal end of the sheath. The legs are movable relative to the sheath to achieve a collapsed position within the sheath and an extended position outside of the sheath in the form of an open basket. The plunger can be moved back and forth between a withdrawn position against the distal end of the sheath with the basket legs in the open position and an extended position away from the distal end of the sheath with the basket legs in a closed position. The distal ends of the legs are farther apart from each other when in the open position than when in the closed position.

27 Claims, 7 Drawing Sheets

U.S. PATENT DOCUMENTS

| | | | |
|---|---|---|---|
| 4,650,466 | 3/1987 | Luther | 604/95 |
| 4,655,219 | 4/1987 | Petruzzi | 128/321 |
| 4,682,599 | 7/1987 | Konomura | 128/328 |
| 4,691,705 | 9/1987 | Okada | 128/328 |
| 4,699,147 | 10/1987 | Chilson et al. | 128/642 |
| 4,706,671 | 11/1987 | Weinrib | 128/348.1 |
| 4,718,419 | 1/1988 | Okada | 128/303.15 |
| 4,723,549 | 2/1988 | Wholey et al. | 128/344 |
| 4,728,319 | 3/1988 | Marsch | 604/22 |
| 4,790,812 | 12/1988 | Hawkins, Jr. et al. | 604/22 |
| 4,790,813 | 12/1988 | Kensey | 604/22 |
| 4,794,928 | 1/1989 | Kletschka | 128/344 |
| 4,807,626 | 2/1989 | McGirr | 128/328 |
| 4,873,978 | 10/1989 | Ginsburg | 128/345 |
| 4,893,621 | 1/1990 | Heyman | 606/127 |
| 4,907,572 | 3/1990 | Borodulin et al. | 606/128 |
| 4,926,858 | 5/1990 | Gifford, III et al. | 606/159 |
| 4,927,426 | 5/1990 | Dretler | 606/128 |
| 4,927,427 | 5/1990 | Kriauciunas et al. | 606/128 |
| 4,994,079 | 2/1991 | Genese et al. | 606/206 |
| 4,998,539 | 3/1991 | Delsanti | 128/898 |
| 5,011,488 | 4/1991 | Ginsburg | 606/159 |
| 5,041,093 | 8/1991 | Chu | 604/104 |
| 5,053,008 | 10/1991 | Bajaj | 604/104 |
| 5,057,114 | 10/1991 | Wittich et al. | 606/127 |
| 5,064,428 | 11/1991 | Cope et al. | 606/127 |
| 5,071,407 | 12/1991 | Termin et al. | 604/104 |
| 5,084,054 | 1/1992 | Bencini et al. | 606/113 |
| 5,098,440 | 3/1992 | Hillstead | 606/108 |
| 5,100,423 | 3/1992 | Fearnot | 606/159 |
| 5,102,415 | 4/1992 | Guenther et al. | 604/159 |
| 5,171,233 | 12/1992 | Amplatz et al. | 604/281 |
| 5,176,688 | 1/1993 | Narayan et al. | 606/128 |
| 5,192,286 | 3/1993 | Phan et al. | 606/127 |
| 5,290,294 | 3/1994 | Cox et al. | 606/108 |
| 5,311,858 | 5/1994 | Adair | 128/4 |
| 5,329,942 | 7/1994 | Gunther et al. | 128/898 |
| 5,330,482 | 7/1994 | Gibbs et al. | 606/113 |
| 5,345,936 | 9/1994 | Pomeranz et al. | 128/642 |
| 5,354,310 | 10/1994 | Garnic et al. | 606/198 |
| 5,376,100 | 12/1994 | Lefebvre | 606/180 |
| 5,421,832 | 6/1995 | Lefebvre | 604/53 |
| 5,496,330 | 3/1996 | Bates et al. | 606/127 |
| 5,499,981 | 3/1996 | Kordis | 606/41 |
| 5,549,626 | 8/1996 | Miller et al. | 606/200 |
| 5,658,296 | 8/1997 | Bates et al. | 606/127 |
| 5,693,069 | 12/1997 | Shallman | 606/205 |

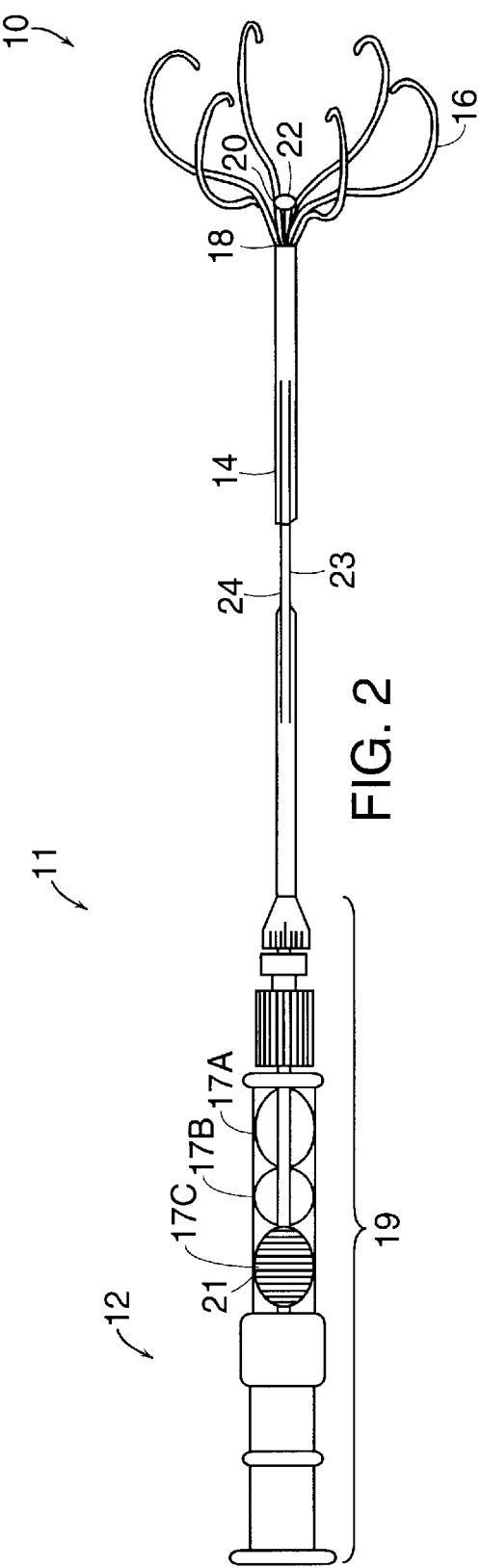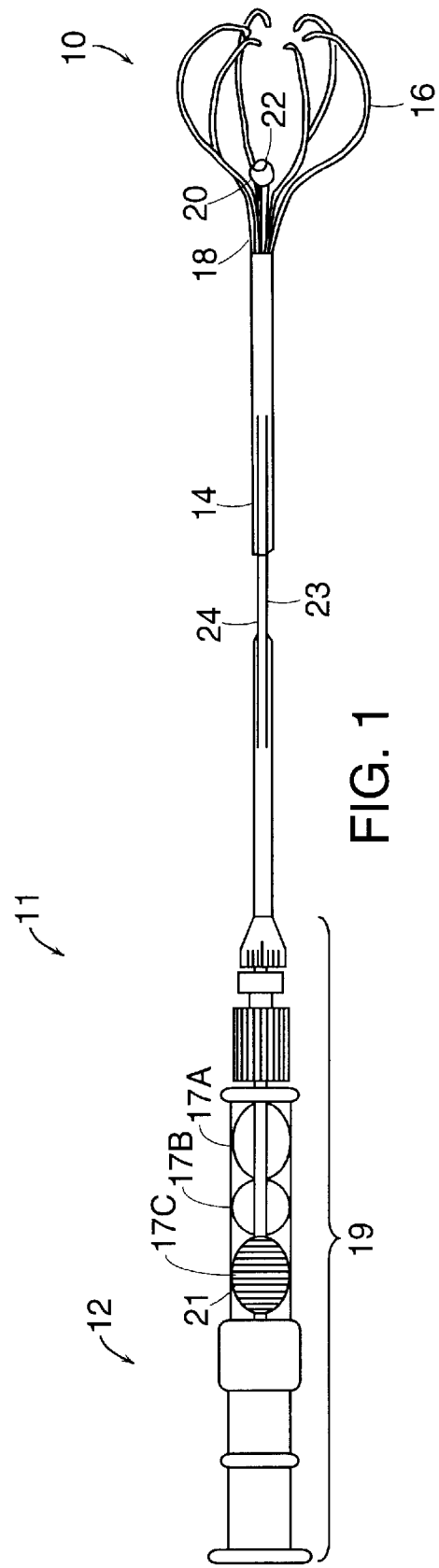

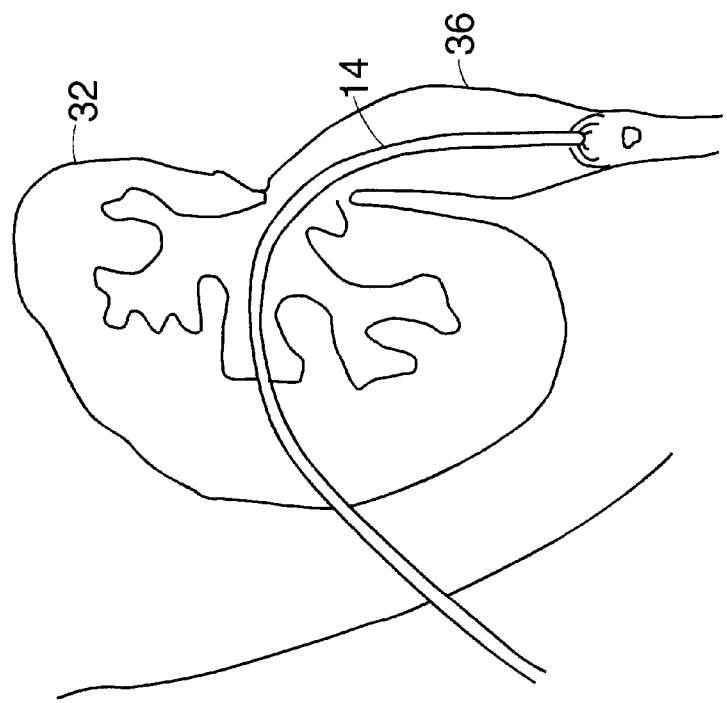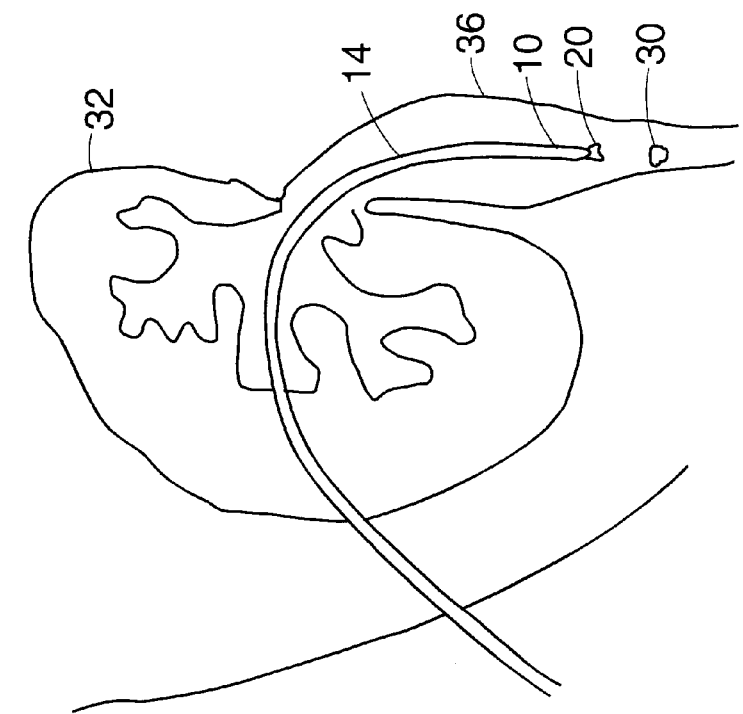
FIG. 7A
FIG. 7B

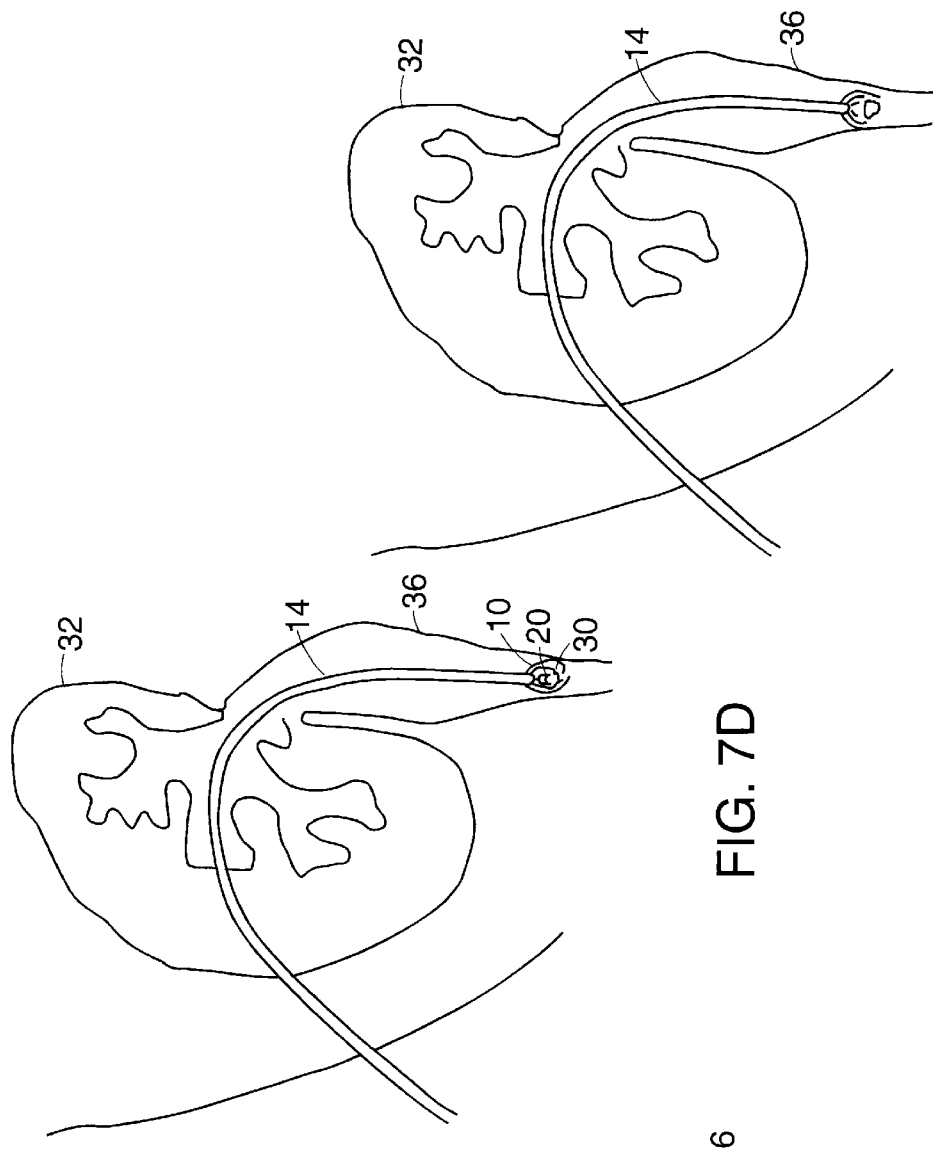
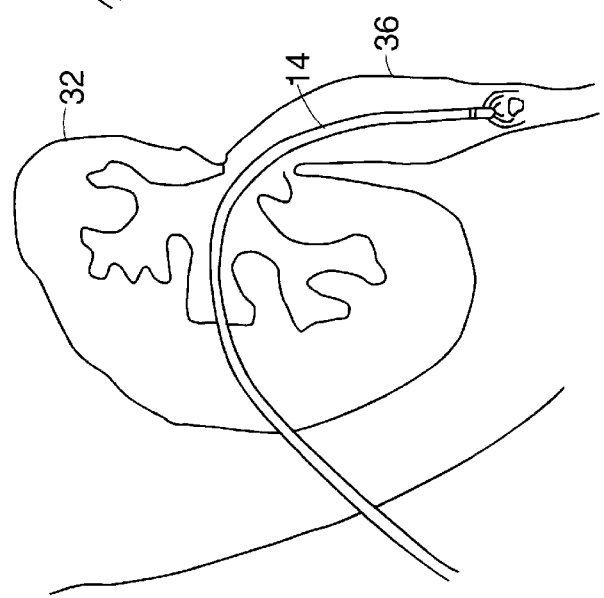
FIG. 7E
FIG. 7D
FIG. 7C

SURGICAL RETRIEVAL BASKET WITH THE ABILITY TO CAPTURE AND RELEASE MATERIAL

TECHNICAL FIELD

The invention relates generally to surgical retrieval devices for removing biological or foreign material from the body. More particularly, the invention relates to a device that has a basket with the ability to capture and release material (e.g., stones, calculi, etc.).

BACKGROUND INFORMATION

Some medical instruments can reduce the invasiveness and potential trauma previously associated with various medical procedures. The removal of stones such as kidney stones, gallstones, and the like from the body is one area where certain instruments are being used with some success. Various instruments can permit the removal of stones and other material from the body without the need for major surgery. Generally, a grasping device is guided through the body to the site of the stone and is used to grasp and remove the stone under the guidance of an endoscope.

Some of these instruments incorporate miniaturized grasping forceps. Others incorporate a retrieval basket as shown and described in U.S. Pat. No. 4,590,938 to Segura et al., U.S. Pat. No. 5,496,330 to Bates et al., and U.S. Pat. No. 5,658,296 to Bates et al. Known devices generally have a wire basket within a sheath, and the basket and the sheath move relative to each other to open and close the basket.

One problem with known baskets is that it often is difficult to remove the basket containing the material from the body without damaging the surrounding tissue and it is not possible to release the captured material from the basket. In some instances, a stone is of such a size that it is incapable of being removed while it is captured within the basket. In other instances, the body duct or orifice, such as the ureter or ureteral orifice junction (where the ureter and bladder join), is too small to allow for passage of the basket with the captured stone. If an excessive force is used to attempt to remove the basket and the captured material, tissue may be damaged. Sometimes surgery is required to dislodge both the basket and the captured material.

SUMMARY OF THE INVENTION

The invention provides a device and method for the retrieval of material from the body. In particular, the instant invention provides a surgical extractor which is capable of capturing and releasing foreign or biological material (e.g. stones, calculi, etc.). The design objectives of the invention are to allow for the both the capture and release of material thereby preventing trauma to the body tissues and to the lining of the lumens of the body and to enhance the ability of the basket to retain the material during removal.

In accordance with the invention, a surgical retrieval device, and related methods, use a basket formed by a plurality of legs to retrieve foreign or biological material. The surgical extractor has a basket which can be moved between an open and closed positions thereby allowing for both the capture and release of material. During removal of captured material from a body, if it should become necessary, it is possible to open the basket and release the material thereby preventing damage to the surrounding tissue and permitting removal of the extractor.

In one aspect, the invention involves a surgical retrieval device. The device comprises a basket, plunger, and a sheath. The basket is comprised of a plurality of legs which are movable relative to the sheath to achieve a collapsed position within the sheath and extended position out of the distal end of the sheath in the form of a open basket. The distal ends of the legs are unattached while the proximal ends join at a base of the basket. The plunger is positioned at the distal end of the sheath and is movable relative to the sheath from a withdrawn position, with an open basket, to an extended position, with a closed basket.

In an embodiment of this aspect of the invention, the plunger and the basket can be connected to an actuating mechanism at the proximal end of the sheath. This mechanism can comprise a slider on a proximal handle, and one or more individual cables can be located within the sheath and operatively attached at each end to the mechanism and the basket and plunger. For example, the actuating mechanism, via a first cable, can move the basket from a retracted position collapsed within the sheath to an advanced position outside of the sheath which causes the basket to self expand to an open position. The actuating mechanism, via a second cable, can move the plunger from a withdrawn position, with an open basket, to an extended position, with a closed basket. The actuating mechanism can include a slider on a handle which controls movement of both the basket and the plunger or, alternatively, it can include two sliders on the handle, one controlling the basket and the other controlling the plunger.

The basket legs can be made of metal (e.g., stainless steel, NiTi ("Nitinol"), etc.) or plastic, and they can be preformed to attain the shape of an open basket when extended. The legs can have a cross-section that is rounded, rectangular, D-shaped with a rounded outer surface and a flat inner surface, or V-shaped with a rounded outer surface and a wedge shaped inner surface. Other cross-sectioned shapes are possible. Also, the inner surface of the legs can comprise a surface that is rougher than the outer surface, and this roughness can comprise, for example, a serrated surface, a toothed surface, or an etched surface. The rough inner surface(s) enhance stone capture and retention.

The plunger, which can be comprised of metal or plastic, can vary in size relative to the sheath. Generally, the width of the plunger is equal to or less than the diameter of the sheath. The plunger can also have a variety of configurations. For example, the plunger can be bell-shaped, cone-shaped, semi-sphere shaped or sphere-shaped. In some embodiments, the plunger has a concave distal surface. In addition, the plunger can have grooves on the outer surface for receiving the basket legs and guiding them as they move in and out of the sheath.

In another aspect, the invention provides a method for retrieving biological or foreign material from the body. The method comprises inserting an extractor into a body. The extractor can be as described above. The method further comprises capturing the material within the basket of the extractor, and then withdrawing the extractor from the body to remove the captured material from the body. If it should become necessary during removal of the captured material from the body, the extractor can release the material to permit removal of the extractor from the body but not the material.

Embodiments of this aspect of the invention can include the following features. The capturing step can comprise capturing a calculus, such as, for example, a kidney stone, a ureteral stone, a urethral stone, a urinary bladder stone, or a stone in the biliary tree such as a gallbladder stone or a bile duct stone.

The foregoing and other objects, aspects, features and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a plan view of a surgical extractor with a handle at a proximal end and a closed retrieval basket at a distal end.

FIG. 2 is a plan view of the surgical retrieval basket of FIG. 1 with an open retrieval basket at the distal end.

FIGS. 7A–7E illustrate a clinical application of a surgical extractor of the invention. For ease of understanding how the extractor operates, the plunger and the basket are shown larger than their actual size.

DESCRIPTION

Figure 3:
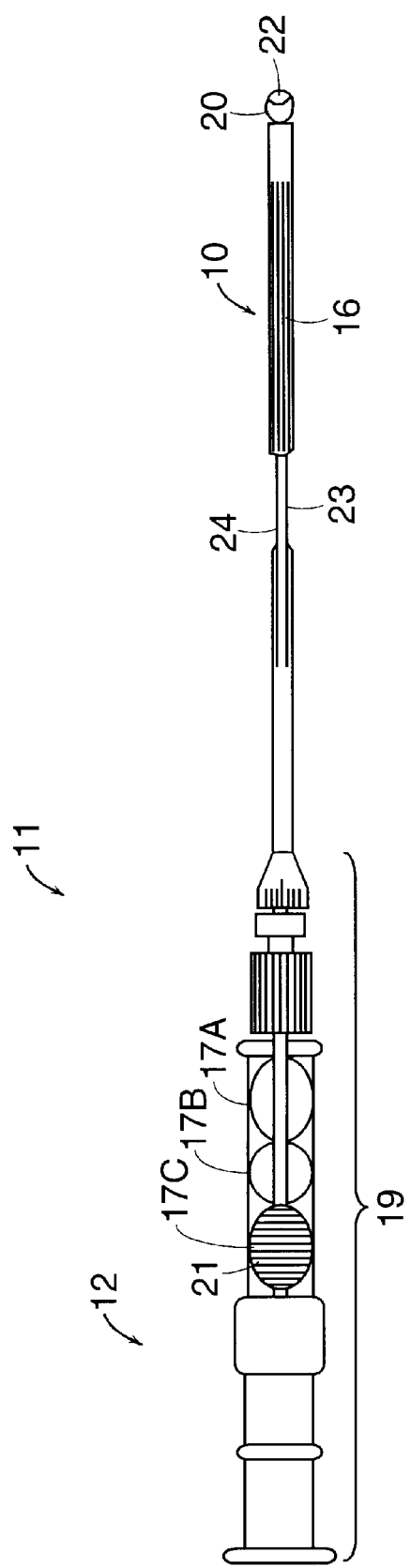
FIG. 3 is a plan view of the surgical retrieval basket of FIG. 1 with the basket in a collapsed position within the sheath.

Referring to FIGS. 1–3, a surgical extractor 11 according to the invention includes a basket 10 for retrieving material (biological or foreign) and a plunger 20 attached to an actuation device 12 via a sheath or catheter 14. The basket 10 includes a plurality of legs (or wires) 16 that are made of any of a variety of materials such as metal (e.g., stainless steel, NiTi ("Nitinol") etc.) or plastic (e.g., Teflon) and that are attached at the base 18 of the basket 10. In general, the basket 10 is formed by a plurality of legs, and it typically is formed by at least three legs. At the base 18 of the basket 10, the legs 16 are attached to a first shaft, coil, cable, or wire 23 located within the sheath 14. Each of the legs 16 is free or unattached at its distal ends, as shown. This first cable 23 is actuated by the actuation device 12 (e.g., a slider 21 on a proximal handle 19) to move the first cable 23 and thus the basket legs 16, and the basket 10 thus is advanced outside of the sheath, as shown in FIG. 2, and retracted within the sheath, as shown in FIG. 3, by use of the actuation device 12. The plunger 20, which is a bell-shaped mechanism made of any of a variety of materials such as metal (e.g. stainless steel, NiTi ("Nitinol"), etc.) or plastic (e.g., Teflon) with a concave distal surface 22 for contacting a stone or other material, extends from the distal end of the sheath 14 and is attached to a second shaft, coil, cable, or wire 24 located within the sheath 14. The width of the plunger 20 is generally equal to or less than the diameter of the sheath 14. This second cable 24 is actuated by the actuation device 12 (e.g., the slider 21 on the proximal handle 19) to move the second cable 24 and thus the plunger 20 from a withdrawn position, with an open basket (as shown in FIG. 2) to an extended position, with a closed basket (as shown in FIG. 1). The second cable can be within its own independent sheath (not shown). There can be an additional slider (not shown) on the proximal handle 19 which independently moves the second cable 24 and thus the plunger 20 from a withdrawn position, with an open basket (as shown in FIG. 2) to an extended position, with a closed basket (as shown in FIG. 1).

In one embodiment, when the slider 21 is moved to its furthest distal position (position 17A), the wire basket 10 is collapsed within the sheath 14 and placed in the position shown in FIG. 3. When the slider 21 is moved proximally to position 17B, the wire basket 10 moves out of the sheath 14 and the basket 10 assumes an open position as shown in FIG. 2. When the slider 21 is moved to its furthest proximal position (position 17C), the plunger 20 extends forward from the distal end of the sheath 14 and the basket legs 16 close around the plunger 20 as shown in FIG. 1. If the slider 21 is now moved back to position 17B, the plunger 20 is withdrawn and the basket 10 is opened. If the slider 21 is now moved back to the furthest distal position (position 17A), the basket is collapsed within the sheath. This is just one possible embodiment of an actuation device 12 useful for opening and closing the basket 10 and operating the plunger 20. One type of handle is disclosed in U.S. Pat. No. 5,496,330 to Bates et al., the entirety of which is incorporated herein by reference. Other mechanisms are possible.

With continued reference to FIGS. 1–3, an operator (e.g., a physician) uses the extractor 11 by introducing at least the distal portion of the extractor 11 into a patient in a form in which the basket 10 is collapsed within the sheath 14. In the collapsed state, the sheath 14 retains the basket 10 in a compact form until the extractor 11 is positioned proximate to material to be retrieved such as, for example, a stone. The operator holding the handle 19 then operates the actuation device 12 to control the first and second cables 23, 24 and consequently the position of the basket 10 and the plunger 20. The positions include the basket 10 fully collapsed within the sheath 14 (as shown in FIG. 3), the basket 10 fully deployed outside of the sheath 14 and open with the plunger 20 withdrawn (as shown in FIG. 2), and the basket 10 deployed outside of the sheath 14 and closed with the plunger 20 extended (as shown in FIG. 1). The operator can use the actuation device 12 to open the retrieval basket 10 via the first cable 23. With the basket 10 fully deployed and extending out of the end of the sheath 14 in the open position with the plunger 20 withdrawn (as shown in FIG. 2), the surrounding tissue of the body lumen or passage in which the basket 10 is disposed is dilated and the basket 10 assumes a three-dimensional structure that can be manipulated over the material (e.g., a stone) to be captured and removed. With the material in close proximity or contacting the concave distal surface 22 of the plunger 20, the operator then closes the legs 16 of the basket 10 around the material by using the actuation device 12 to move the second cable 24 and consequently advance the plunger 20 distally away from the distal end of the sheath 14 which results in the basket legs 16 being released and returning to the closed position (as shown in FIG. 1). The legs 16 return to the closed position when the plunger 10 is extended due to the preformed configuration of the wires to attain the shape of a basket. The legs 16 can be made of a material (e.g., stainless steel, NiTi ("Nitinol"), etc.) that has springiness or memory such that they return to their normally closed position when released. The plunger 20 with its concave distal surface 22 constrains movement of the material within the basket 10 and prevents the material from slipping out of the basket 10. The operator can withdraw the basket legs 16 slightly to more securely grasp the material. The operator can then withdraw the extractor 11 with the entrapped material from the body. During removal, if resistance is encountered, the operator can operate the activation device 12 to withdraw the plunger 20 from the extended position (as shown in FIG. 1) to the withdrawn position (as shown in FIG. 2), which opens the basket 10 and allows for the release of the material. The operator can then operate the actuation device 12 to regrasp the material or to retract the basket 10 into the fully collapsed position within the sheath (FIG. 3) such that the surgical extractor 11 can be removed from the body without causing trauma to the body tissue.

Figure 4A:
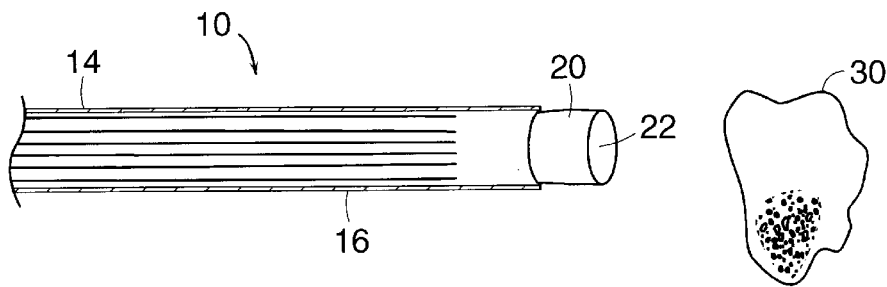
FIGS. 4A–4C are enlarged views of the distal end of the surgical extractor of FIG. 1 showing the basket in the proximity of a stone with the basket being in a collapsed, open (plunger withdrawn), and closed (plunger extended) position, respectively. For ease of understanding how the extractor operates, the plunger is shown larger than its actual size.
Figure 4B:
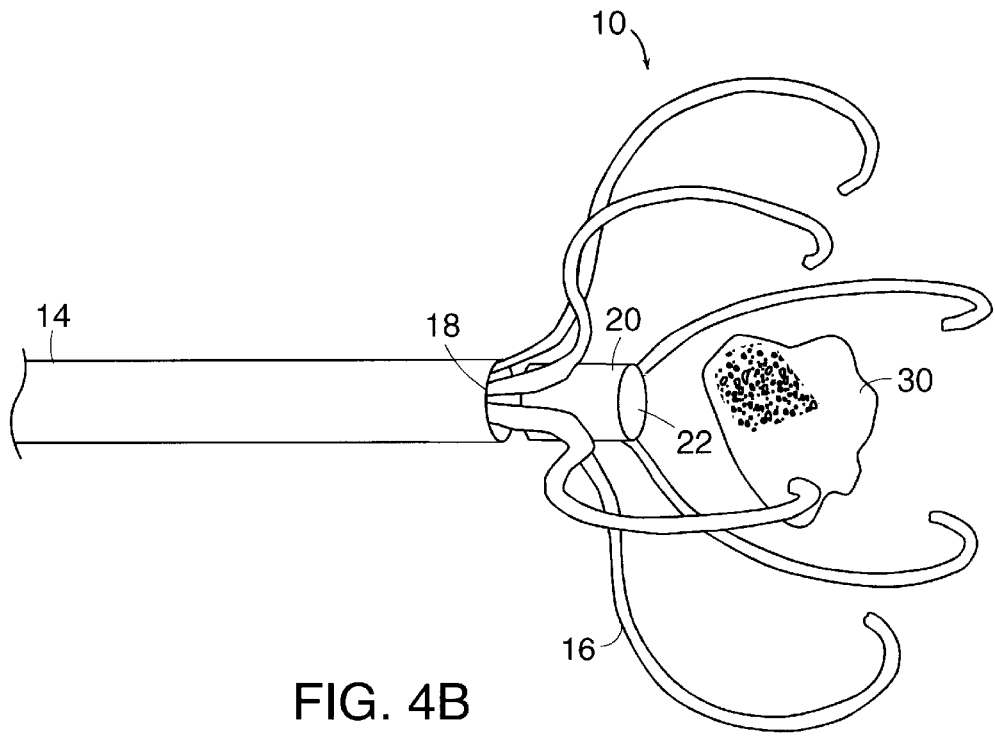
Figure 4C:
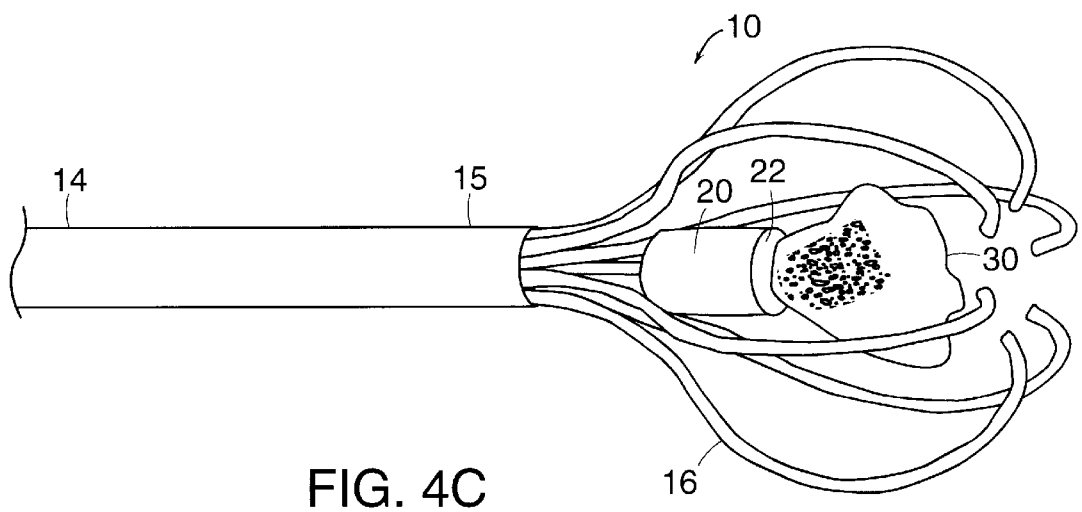

For ease of understanding how the extractor operates, FIGS. 4A–4C illustrate the plunger in an enlarged form. Referring to FIG. 4A, the basket legs 16 are collapsed within the sheath 14 so that the basket 10 assumes a reduced profile corresponding to the diameter of the sheath 14 and the plunger 20 is drawn up against the distal end of the sheath 14 in the withdrawn position. As shown in FIG. 4B, relative movement between the sheath 14 and the legs 16 of the basket 10 extends the legs 16 out from the distal opening of the sheath 14 around the plunger 20 while the plunger 20 remains in the withdrawn position so that the entire basket 10 is outside of the sheath 12 and the basket legs 16 self expand to an open position. As shown in FIG. 4C, once a stone 30 is within the basket 10, the plunger 20 is moved forward distally from the distal opening of the sheath 14 toward the stone 30 and assumes an extended position, and the basket legs 16 close around the stone 30 to secure it against the concave distal surface 22 of the plunger 20. The basket legs 16 are then withdrawn slightly to more securely grasp the stone 30 within the basket 10. The stone 30 can be released from the basket 10 if necessary, and to release the captured stone 30 the plunger 20 is simply moved back toward the sheath 14 to the withdrawn position and the basket legs thus open (as shown in FIG. 4B) and release the stone 30 from the basket 10.

The stone 30 can be any biological or foreign material. For example, it can be a kidney stone, ureteral stone, urethral stone, bladder stone, gallbladder stone, choletith or bile duct stone.

Figure 5A:
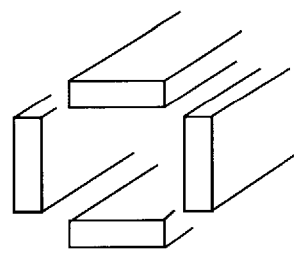
FIGS. 5A–5D are examples of various possible cross sections of legs used to form a basket according to the invention, namely rectangular, round, D-shaped, and V-shaped, respectively.
Figure 5B:
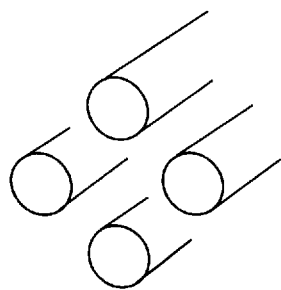
Figure 5C:
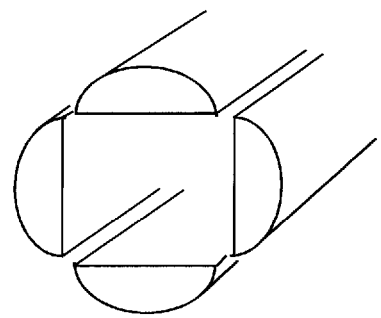
Figure 5D:
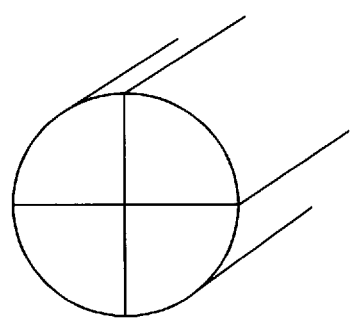

The legs or wires 16 which form the basket 10 can be constructed to have various cross-sectional shapes including, but not limited to, rectangular (FIG. 5A), round (FIG. 5B), D-shaped with a rounded outer surface and a flat inner surface (FIG. 5C), or V-shaped with a rounded outer surface and a wedge-shaped inner surface (FIG. 5D). Furthermore, the inner surface of any of the legs 16 of the basket 10 can comprise a surface that is rougher that the outer surface so as to enhance the grasping and retention ability of the basket. The inner surface can be rough along the entire length of one or more basket legs or for only a portion of the basket leg(s). The roughness can be achieved in a variety of ways including the creation of serrations, teeth, or pitting by, for example, etching, sand blasting, or a variety of other known techniques.

Figure 6A:
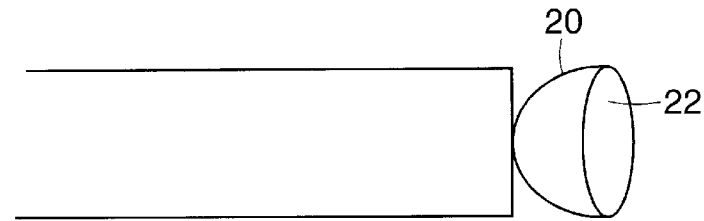
FIGS. 6A–6D are examples of various configurations of the plunger according to the invention, namely, a bell, a cone, a semi-sphere and a sphere-shaped mechanism, respectively.
Figure 6B:
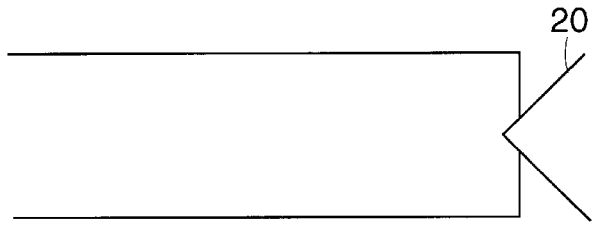
Figure 6C:
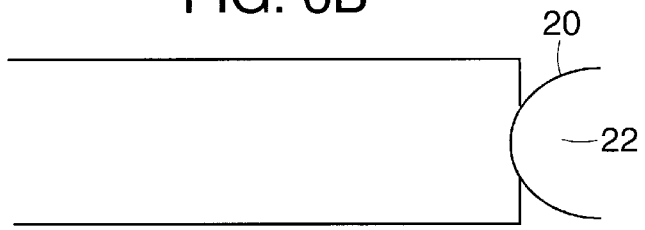
Figure 6F:
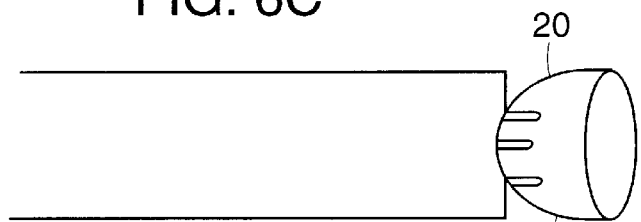
FIG. 6F is an example of a plunger which has grooves on the outer surface for the basket legs.
Figure 6E:
FIG. 6E is an example of a plunger which is smaller that the plungers depicted in 6A–6C.
Figure 6D:

The plunger 20 controls the opening and closing of the basket legs 16. Specifically, when the plunger 20 is withdrawn, the legs 16 are spread apart to an open position and, when the plunger 20 is extended, the basket legs 16 assume a closed position. The plunger 20 also constrains movement of captured material during removal. The plunger 20 can have various shapes including, but not limited to, bell-shaped (FIG. 6A), cone-shaped (FIG. 6B), semi-sphere shaped (FIG. 6C), or sphere-shaped (FIG. 6D). As shown in FIG. 6A and FIG. 6C, in some embodiments, the plunger 20 has a concave distal surface which aids in constraining the entrapped material during removal. The size of the plunger 20 relative to the extractor 11 can also vary to accommodate different size material. Generally, the width of the plunger 20 is equal to or less than the diameter of the sheath 14. As shown in FIG. 6E, the plunger 20 can be small in size allowing it to be retracted within the sheath 14. Furthermore, as shown in FIG. 6F, the outer surface of the plunger 20 can comprise a surface with grooves 42. Each groove 42 receives a basket leg 16 and guides it as it moves in and out of the sheath 14 under operator control.

FIGS. 7A–7E illustrate an application of a basket according to the invention in a clinical setting. For ease of understanding how the extractor operates, the basket 10 and the plunger 20 are shown larger than their actual size. The operator, typically under endoscope guidance, inserts the surgical extractor 11 (with the basket 10 retracted within the sheath 14) into the body and advances the distal end into the kidney 32 or the portion/tract of the body where the stone 30 or material is located, as shown in FIG. 7A. Once the distal end of the sheath 14 is positioned close to the stone 30, the operator extends the basket 10 from sheath 14 and the legs 16 of the basket 10 extend from the distal end of the sheath 14 around the plunger 20 and the basket 10 assumes an open position, as shown in FIG. 7B. The basket 10 is then maneuvered around the stone 30 until the stone 30 is within the basket 10, as shown in FIG. 7C. The operator then extends the plunger 20 from the distal end of the sheath 14 from a withdrawn position (shown in FIGS. 7B and 7C) to an extended position and the legs 16 of the basket 10 close around the stone 30 entrapping the stone 30 against the plunger 20 and the basket 10 assumes a closed position (as shown in FIG. 7D). The operator then withdraws the basket legs 16 slightly to more securely grasp the stone 30. Once the stone 30 is securely entrapped within the basket 10, the surgical extractor 11 is removed from the kidney 32 or other body tract by withdrawing the extractor 11 from the body along the same path used to advance the extractor 11 into the body. If the operator has difficulty removing the stone 30 (for example, the stone is too large), the stone 30 can be released from the basket 10. To the release the stone 30, the operator moves the plunger 20 back toward the sheath 14 to a withdrawn position and the basket legs 16 open allowing for the release of the stone 30, as shown in FIG. 7E. If necessary for removal, the operator can further withdraw the basket 10 into a collapsed position within the sheath 14 (FIG. 7A). The operator can then withdraw the extractor 11 from the kidney 32 or tract. While the application disclosed in FIGS. 7A–7E involves accessing the stone 30 from the outside of the body, through the kidney 32, and into the ureter 36, it is possible to access such a stone by a less invasive path such as inserting the extractor 11 through the urethra into the bladder, and into the ureter 36.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A surgical extractor, comprising:
    a sheath having a proximal end, a distal end and, a hollow passageway within the sheath that extends from the proximal to the distal end;
    a plurality of legs movable relative to said sheath to achieve a collapsed position within said sheath and an extended position out of the distal end of said sheath, the legs forming a basket structure when in the extended position and being unattached at a distal end of the basket structure and joined at a proximal base of the basket structure; and
    a plunger disposed at the distal end of said sheath and movable relative to the sheath to allow said legs, when in the extended position, to move from an open position to a closed position, wherein the unattached ends of the legs are farther apart from each other when in the open position than when in the closed position.

2. The extractor of claim 1 further comprising an actuating mechanism disposed at the proximal end of the sheath.

3. The extractor of claim 2 wherein said actuating mechanism moves the plunger and the legs.

4. The extractor of claim 1 wherein the legs have a round cross-section.

5. The extractor of claim 1 wherein the legs have a rectangular cross-section.

6. The extractor of claim 1 wherein the legs have a D-shaped cross-section.

7. The extractor of claim 1 wherein the legs have a V-shaped cross-section.

8. The extractor of claim 1 wherein at least a portion of an inner surface of at least one of the legs is rough.

9. The extractor of claim 8 wherein the rough inner surface comprises a serrated surface.

10. The extractor of claim 8 wherein the rough inner surface comprises a toothed surface.

11. The extractor of claim 8 wherein the rough inner surface comprises an etched surface.

12. The extractor of claim 1 wherein the legs comprise metal.

13. The extractor of claim 12 wherein the legs comprise stainless steel.

14. The extractor of claim 12 wherein the legs comprise NiTi.

15. The extractor of claim 1 wherein the legs comprise a plastic material.

16. The extractor of claim 1 wherein the legs are preformed to attain the open position of the basket structure.

17. The extractor of claim 1 wherein said plunger has a concave distal surface.

18. The extractor of claim 1 wherein said plunger comprises a bell shape.

19. The device of claim 1 wherein said plunger comprises a cone shape.

20. The device of claim 1 wherein said plunger comprises a sphere shape.

21. The device of claim 1 wherein said plunger has grooves on its outer surface for the basket legs.

22. A method of retrieving material from a body, comprising:
    inserting a surgical extractor into the body, the extractor including a sheath and a basket which is movable relative to the sheath between a collapsed position within the sheath and an extended position out of a distal end of the sheath, the basket being formed by a plurality of legs which are unattached at a distal end of the basket and joined at a proximal base of the basket, the extractor also including a plunger positioned at the distal end of said sheath,
    positioning said extractor proximate to material to be removed with the plunger in a withdrawn position and the basket legs deployed outside the sheath in an open position with the unattached legs of the distal end of the basket positioned apart from each other,
    advancing the plunger distally away from the distal end of the sheath to cause the basket legs to close around said plunger and the material,
    withdrawing said extractor from the body with the material entrapped within the basket, and
    releasing the material from the basket by retracting said plunger to a withdrawn position which causes said basket legs to open and allows release of the material.

23. The method of claim 22 wherein the step of capturing the material comprises capturing a calculus.

24. The method of claim 22 wherein the step of capturing the material comprises capturing a kidney stone.

25. The method of claim 22 wherein the step of capturing the material comprises capturing a ureteral stone.

26. The method of claim 22 wherein the step of capturing the material comprises capturing a bladder stone.

27. The method of claim 22 wherein the step of capturing the material comprises capturing a stone in the biliary tree.

* * * * *

UNITED STATES PATENT AND TRADEMARK OFFICE
CERTIFICATE OF CORRECTION

PATENT NO. : 5,944,728
DATED : August 31, 1999
INVENTOR(S) : Bates

It is certified that error appears in the above-identified patent and that said Letters Patent is hereby corrected as shown below:

On the title page:

The Assignee in item: [73] "Boston Scientific Corporation, Natick, Mass." should be replaced with --SCIMED Life Systems, Inc., Maple Grove, Minn.--.

Signed and Sealed this

Twenty-ninth Day of August, 2000

Attest:

Q. TODD DICKINSON

*Attesting Officer*

*Director of Patents and Trademarks*